(12) United States Patent
Sassoon

(10) Patent No.: US 7,320,418 B2
(45) Date of Patent: Jan. 22, 2008

(54) CONTROLLABLE DOOR HANDLE SANITIZER SYSTEM AND METHOD

(75) Inventor: Simon Sassoon, New York, NY (US)

(73) Assignee: HYSO Technology LLC, New York, NY (US)

( * ) Notice: Subject to any disclaimer, the term of this patent is extended or adjusted under 35 U.S.C. 154(b) by 29 days.

(21) Appl. No.: 11/476,465

(22) Filed: Jun. 27, 2006

(65) Prior Publication Data

US 2006/0243762 A1 Nov. 2, 2006

Related U.S. Application Data

(63) Continuation of application No. 11/104,292, filed on Apr. 11, 2005.

(60) Provisional application No. 60/642,792, filed on Jan. 10, 2005.

(51) Int. Cl.
*G04C 23/42* (2006.01)

(52) U.S. Cl. ............................ 222/649; 222/1; 222/52; 222/63; 222/180; 222/181.3; 222/504; 222/645; 222/402.1; 422/28

(58) Field of Classification Search .................... 222/1, 222/52, 61, 63, 644–645, 649, 180, 181.3, 222/183, 402.1, 160, 402.2, 504, 509, 192, 222/325; 422/28; 16/904
See application file for complete search history.

(56) References Cited

U.S. PATENT DOCUMENTS

| | | | |
|---|---|---|---|
| 1,491,780 A | 4/1924 | Abbott | |
| 1,783,097 A | 11/1930 | Polcari | |
| 2,527,955 A | 10/1950 | Pagel | |
| 3,314,746 A | 4/1967 | Millar | |
| 3,610,471 A | 10/1971 | Werner | |
| 3,615,041 A | 10/1971 | Bischoff | |
| 3,732,509 A | 5/1973 | Florant et al. | |
| 3,994,440 A * | 11/1976 | Mancini | ...................... 239/274 |
| 4,064,573 A | 12/1977 | Calderone | |
| 4,171,776 A | 10/1979 | Pagliaro | |
| 4,625,342 A * | 12/1986 | Gangnath et al. | ............ 4/228.1 |
| 4,832,942 A | 5/1989 | Crace | |
| 5,016,781 A | 5/1991 | Ten Wolde et al. | |
| 5,031,252 A | 7/1991 | Oyama et al. | |
| 5,314,668 A | 5/1994 | Biermaier et al. | |
| 5,695,091 A | 12/1997 | Winings et al. | |
| 5,808,553 A | 9/1998 | Cunningham | |
| 5,887,759 A | 3/1999 | Ayigbe | |
| 6,123,268 A | 9/2000 | Chastine | |

(Continued)

*Primary Examiner*—Frederick C. Nicolas
(74) *Attorney, Agent, or Firm*—Darby & Darby PC

(57) ABSTRACT

Controlled sanitizing by dispensing a germicide, such as a disinfectant, antibacterial solution or cleansing agent at intervals. A system can include a housing sized to seat an aerosol can and a control circuit that operates to momentarily open a valve on the aerosol can through action of a gear system upon an aerosol delivery tube. A sensor responds to displacement of the delivery tube to deliver state signals to the control circuit. The control circuit prevents action of the gear system in the event that the state signals fail at least one prescribed condition. A method registers at least the displacement of the delivery tube via the sensor and prevents subsequent displacements and hence subsequent sanitizing in the event that the sensor has not registered at least the displacement of the delivery tube. The method ensures that a suitable aerosol can has been properly loaded in the dispenser.

16 Claims, 11 Drawing Sheets

U.S. PATENT DOCUMENTS

| | | |
|---|---|---|
| 6,264,548 B1 | 7/2001 | Payne, Jr. et al. |
| 6,279,777 B1 | 8/2001 | Goodin et al. |
| 6,298,521 B1 | 10/2001 | Butterfield |
| 6,645,435 B2 | 11/2003 | Dawson et al. |
| 6,789,695 B1 | 9/2004 | Gaudreau |
| 6,874,697 B2 | 4/2005 | Callueng |
| 2004/0026530 A1 | 2/2004 | Callueng |
| 2005/0112022 A1 | 5/2005 | Morgan |

* cited by examiner

CONTROLLABLE DOOR HANDLE SANITIZER SYSTEM AND METHOD

RELATED APPLICATIONS

This application claims the benefit of priority under 35 U.S.C. § 120 as a continuation-in-part of PCT Application Serial No. PCT/US2006/00841, filed Jan. 9, 2006, entitled "Door Handle Sanitizer System And Valve Attachment Apparatus," which is a continuation-in-part of U.S. application Ser. No. 11/104,292, filed Apr. 11, 2005, entitled "Door Handle Sanitizer System and Apparatus," which in turn claims priority under 35 U.S.C. § 119(e) of U.S. Provisional Application Ser. No. 60/642,792, filed Jan. 10, 2005, entitled "Door Handle Sanitizer System and Apparatus." The entire disclosure of each of the aforementioned priority applications are hereby incorporated by reference.

FIELD OF THE INVENTION

The present invention relates to an apparatus and method for rendering germ-free (sanitizing) door handles, and more particularly, to a device for dispensing a germicide, such as a disinfectant, antibacterial solution or cleansing agent, onto a door handle at controlled intervals and to a valve attachment suitable for use therewith.

BACKGROUND OF THE INVENTION

Many people are reluctant to use public restrooms due to actual or perceived sanitary conditions of those restrooms. However, in some instances, such use is unavoidable.

These people try to avoid touching any surface after they have washed their hands. However, touching a surface of the restroom is nearly unavoidable because sometimes the person must touch the handle of the door to exit the restroom. Some people carry gloves, wipes or the like to use in such public restrooms. Some people take an extra paper towel to use to cover the door handle. All of these techniques work, but are burdensome and not efficient.

Some prior art methods suggest covering a handle of a door so a person opening the door can avoid direct contact with the handle. Covering a door handle, while effective in preventing a person from contacting the door handle during operation of the door, does little to clean or disinfect the door handle. Furthermore, the cover then becomes a source of contamination, germs, bacteria and the like. Therefore, there is a need for efficiently and effectively sanitizing the handle of a door. This typically requires a person to carry a liquid spray bottle into a room, spray a disinfectant or antibacterial liquid onto the door handle and then wipe the handle clean. This procedure can be cumbersome and inefficient, requiring a person to carry items with him or her for the cleaning procedure.

Still further, some people, often nicknamed germephobes, wonder when the last time a door handle was cleaned, and even if there is some form of protection for this person, they are uncomfortable touching the door handle. These people are not satisfied by the mere existence of some means for cleaning or sanitizing the door handle, rather, they might prefer to know that such a cleansing device is activated at intervals in response to certain conditions or according to a prescribed cleaning schedule, such as every several minutes. Therefore, there is a need for efficiently cleaning and sanitizing a door handle at prescribed time intervals in response to certain conditions, e.g., according to a predetermined cleaning schedule, opening and closing of the door, passing of an individual in the vicinity of the door knob, turning on/off of the lights, etc. There is also a need to control the door handle sanitizing device to automatically shutdown during times when the door is not in use, e.g., overnight, weekends, and any other prescribed time when the door is not being use for an extending period.

SUMMARY OF THE INVENTION

In accordance with one aspect of the invention, a door handle sanitizer for disinfecting a door handle includes a source of liquid or gaseous disinfectant, a spray nozzle configured to convey liquid or gaseous disinfectant from the source to the nozzle and for dispensing the liquid or gaseous disinfectant onto the handle, and a controller for causing the liquid or gaseous disinfectant to be conveyed to the handle in intervals, wherein the intervals are responsive to an external condition and the controller if free of any manual activation.

In accordance with another aspect of the invention, the door handle sanitizer includes a mount suitable to connect the sanitizer to the door. The spray nozzle is configured to convey a prescribed amount of the liquid or gaseous disinfectant from the source to the nozzle and dispense the prescribed amount of liquid or gaseous disinfectant onto the handle.

According to yet another aspect of the present invention, the controller includes a timing circuit which activates the spray nozzle to dispense the liquid or gaseous disinfectant at prescribed time intervals on the basis of a predetermined cleaning cycle of the door handle sanitizer.

According to a further aspect of the invention, a method for sanitizing the door handle includes the steps of mounting the door handle sanitizer proximate the door handle and spraying a germicide as an atomized mist from the dispenser onto the door handle in response to an event free of any manual activation.

According to a further aspect of the invention, an attachment for the valve of an aerosol can is disclosed. The attachment includes a hollow tube having first and second ends, the first end shaped to seat on the valve of the aerosol can and the second end, opposite the first end. The attachment further includes a nozzle disposed adjacent the second end and disposed in fluid communication with the first end via the hollow tube. The nozzle dispersing any aerosol therefrom in a pattern. A bearing surface is disposed along the hollow tube, as well as, an exterior feature which moves in synchronization with the bearing surface. A frangible joint, such as, a score or break-line, is disposed between the first end and the exterior feature.

The above described attachment is usable in a system for sanitizing door handles using sanitizer in an aerosol can having a valve. The door handle sanitizing system includes: a housing sized to seat the aerosol can therein; a motor; an attachment rigidly and fluidly connected to the valve of the aerosol can, the attachment having a first end shaped to seat on the valve and a second end opposite the first end; a first gear system coupled to the motor and operative to momentarily displace the attachment and open the valve; a second gear system driven in response to displacement of the attachment; and a shutter connected to the second gear system and having a rest position and a displaced position, wherein the shutter moves between the rest and displaced positions.

These and further aspects, features and advantages of the present invention will become more apparent from the following detailed description when taken in connection with the accompanying drawings which show, for purposes of illustration only, a preferred embodiment of the present invention.

BRIEF DESCRIPTION OF THE DRAWINGS

The present invention is illustrated by way of example and not by way of limitation in the figures of the accompanying drawings in which like references indicate similar elements.

DETAILED DESCRIPTION OF CERTAIN EMBODIMENTS

Figure 1:
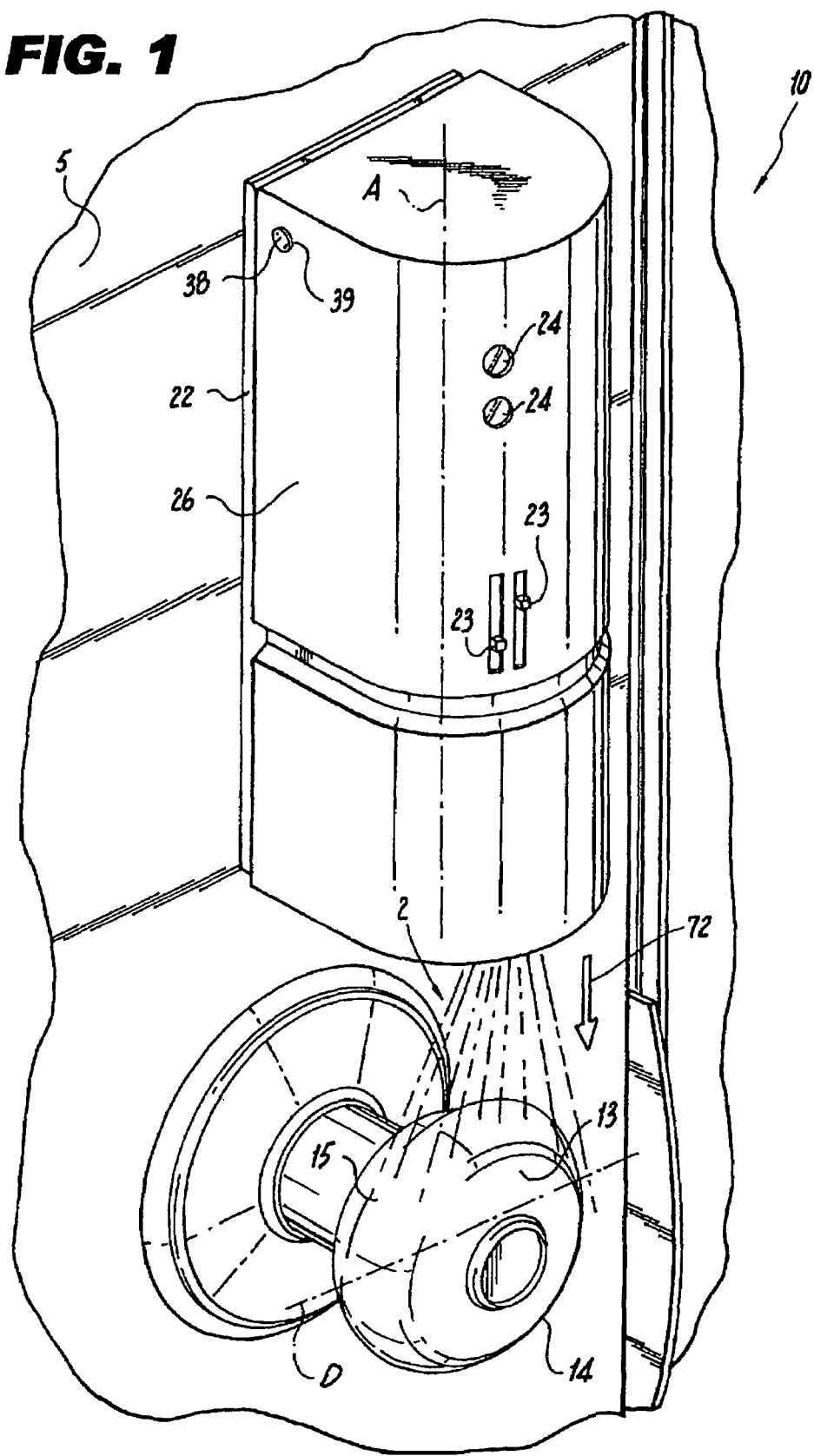
FIG. 1 is a perspective view a door handle sanitizer according to a first embodiment of the present invention mounted on a door above the door handle.
Figure 2:
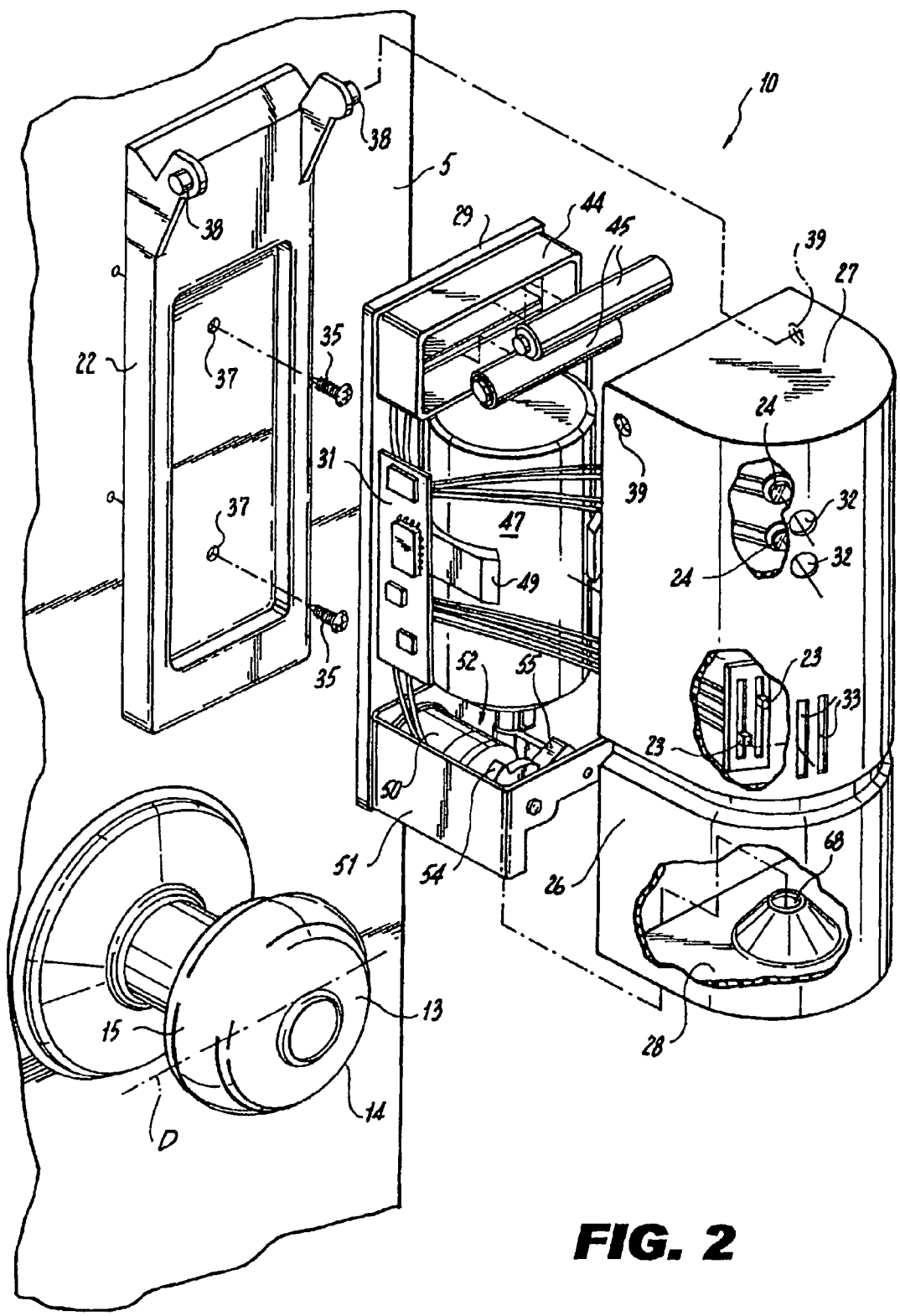
FIG. 2 is a perspective exploded view of the door handle sanitizer of FIG. 1.

FIG. 1 illustrates a perspective view of a door 5 equipped with a spray dispenser 10 in accordance with a first embodiment of the present invention. Spray dispenser 10 is operable to spray a germicide 2 therefrom to coat, and thereby sanitize, an outwardly extended door handle 14. FIG. 2 illustrates an exploded view of the dispenser 10.

Referring to FIGS. 1 and 2, spray dispenser 10 includes an outer housing 21, base 22, user accessible control switches 23 and visible indicator lights 24 for providing control and status information of dispenser 10.

Spray dispenser 10 is preferably mounted to door 5 above door handle 14 as indicated. Outer housing 21 is hingedly connected to base 22 via prongs 38. Prongs 38 are configured to fit through orifices 39 of housing 21 and allow for rotational movement of the outer housing 21 between a close and opened position. In a closed position, outer housing 21 completely conceals the internal components of dispenser 10, while in an opened position, outer housing 21 provides access to germicide source 47 as well as other internal components contained within dispenser 10, such as batteries 45.

Outer housing 21 of spray dispenser 10 comprises a top wall 27, a bottom wall 28 and, for the purpose of presenting a pleasant appearance, a curved front wall 26. Dispenser 10 also includes a component support wall 29 to which the majority of the internal components of spray dispenser 10 are attached.

A germicide source 47, preferably in the form of an aerosol can, is removably mounted within spray dispenser 10. Specifically, with reference to FIG. 3, germicide source 47 is retained by a mounting bracket 49 which functions to secure germicide source 47 in place and align its nozzle (valve 57) with elongated nozzle 56 of spray actuator 52. Mounting bracket 49 also provides an efficient means for removal of germicide source 47 in the event replacement is necessary. As illustrated, mounting bracket 49 is preferably U-shaped having a base portion 81 and two arms 83 extending therefrom for securing germicide source 47 therebetween. Base portion 81 is fixed to component support wall 29. Mounting bracket 49 should have flexible properties such that arms 83 are capable of flexing widthwise to allow insertion of germicide source 47 within the confounds of the arms, while also maintaining their shape so as to completely support the weight of germicide source 47. Accordingly, germicide source 47 can "snap in" and "out" of bracket 49 with minimal force and without causing damage to either the bracket of the germicide source and, as stated above, should be sufficient to secure germicide source 47 in place within spray dispenser 10 without the need for additional securing mechanisms. One of ordinary skill in the art would realize that various alternative mounting devices can be employed for securing germicide source within spray dispenser 10, e.g., Velcro straps, ties, belts, clamps, etc., and a spray dispenser 10 according to present invention can be readily adapted to function with any such alternative securing device.

A motor 50, gear 54, arm 55, elongated nozzle 56 and spring 57, herein collectively referred to as the spray actuator 52, are supported within a motor mount bracket 51. Motor mount bracket 51, as with mounting bracket 49 described above, is also fixedly attached to component support wall 29. When outer housing 21 is in a closed position both mounting brackets 51 and 49, germicide source 47 and spray actuator 52 are all shielded from view under the cover of outer housing 21. The relationship between the individual components of spray actuator 52 and their operation in mechanically effecting the release of germicide 2 from source 47 will now be described in detail with reference to FIGS. 3-5.

Figure 3:
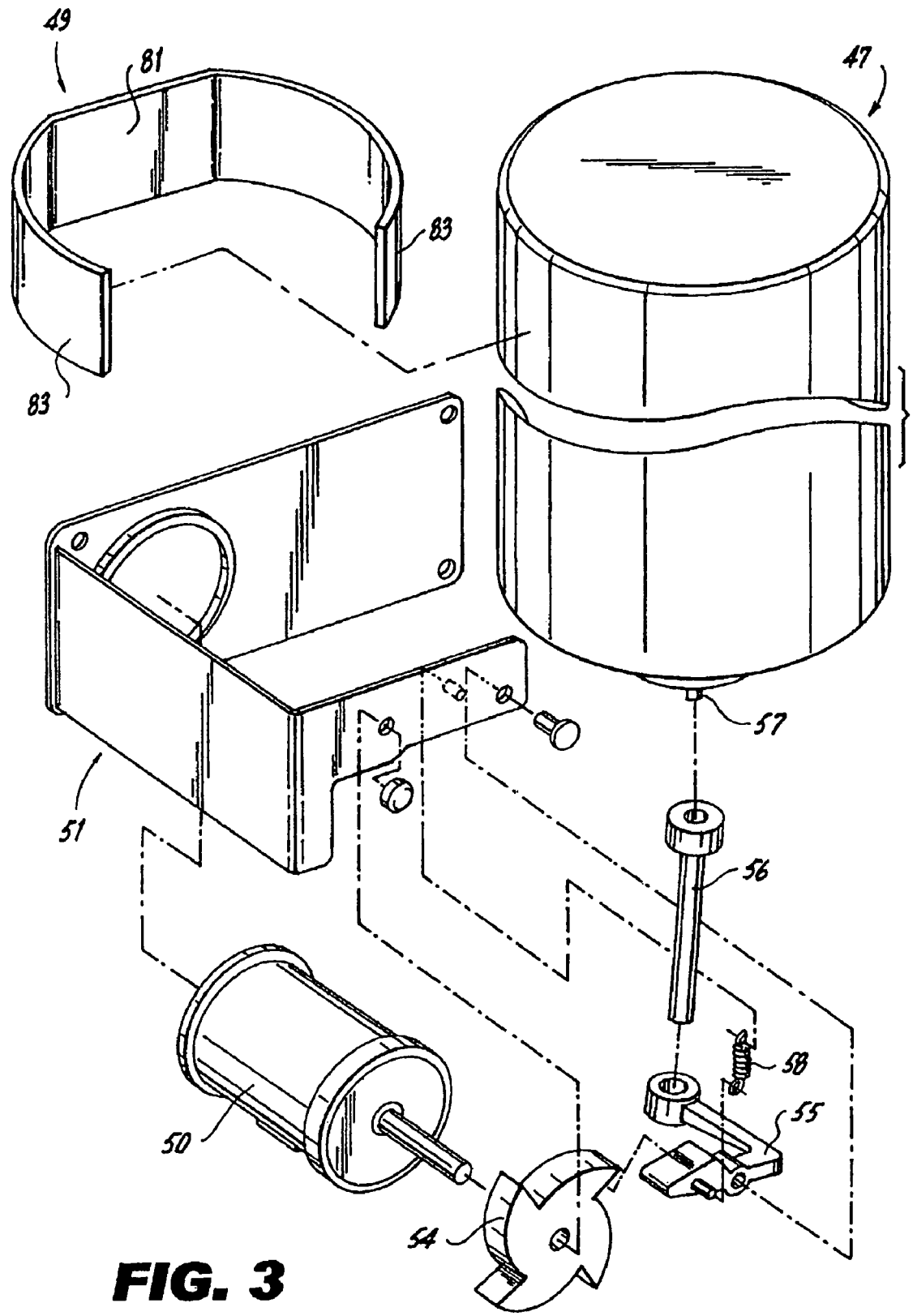
FIG. 3 is an enlarged view of a germicide source and spray actuator of the sanitizer of FIG. 1.
Figure 4:
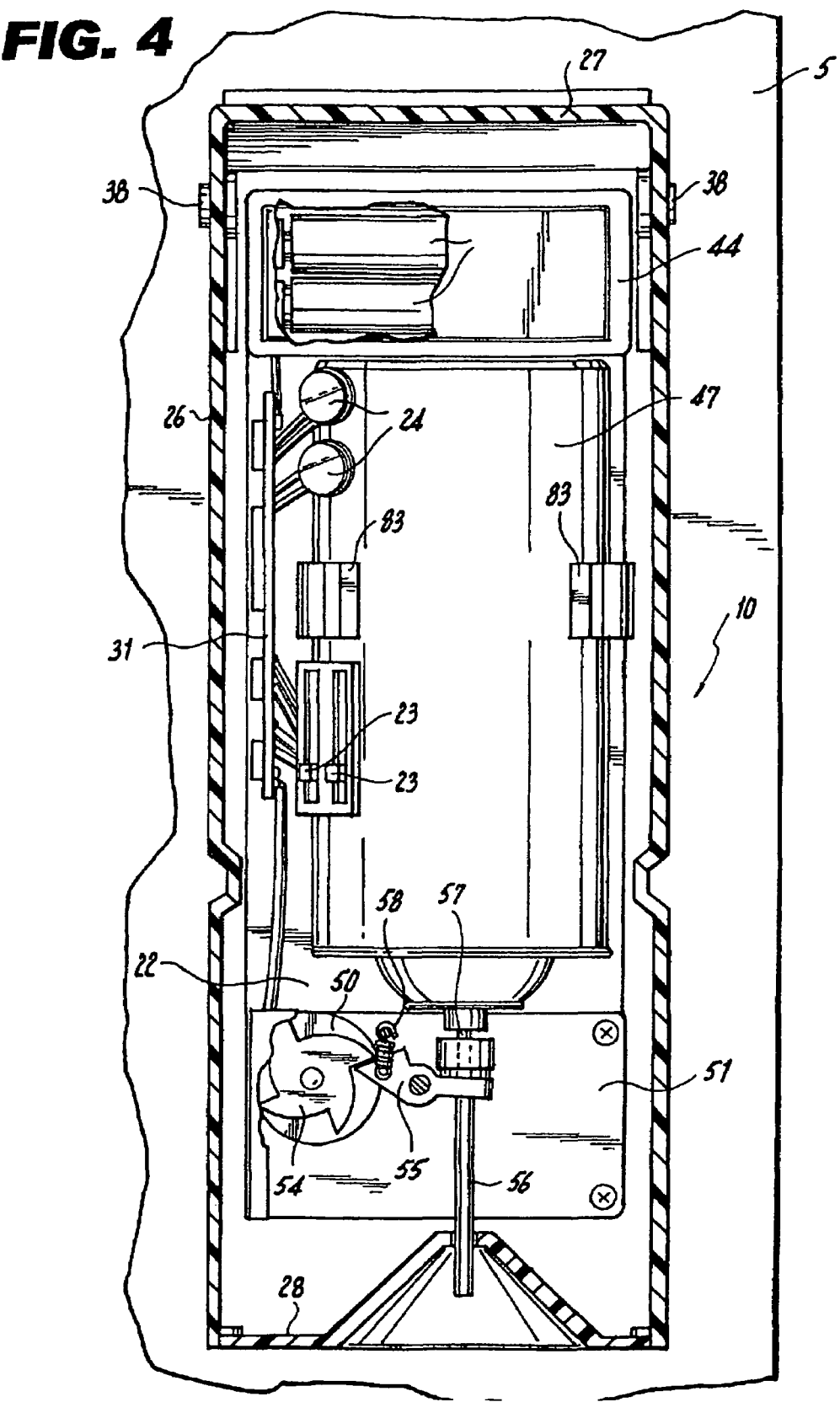
FIG. 4 is a front elevation view of the door handle sanitizer of FIGS. 1-2 absent the outer cover to show interior components.
Figure 5:
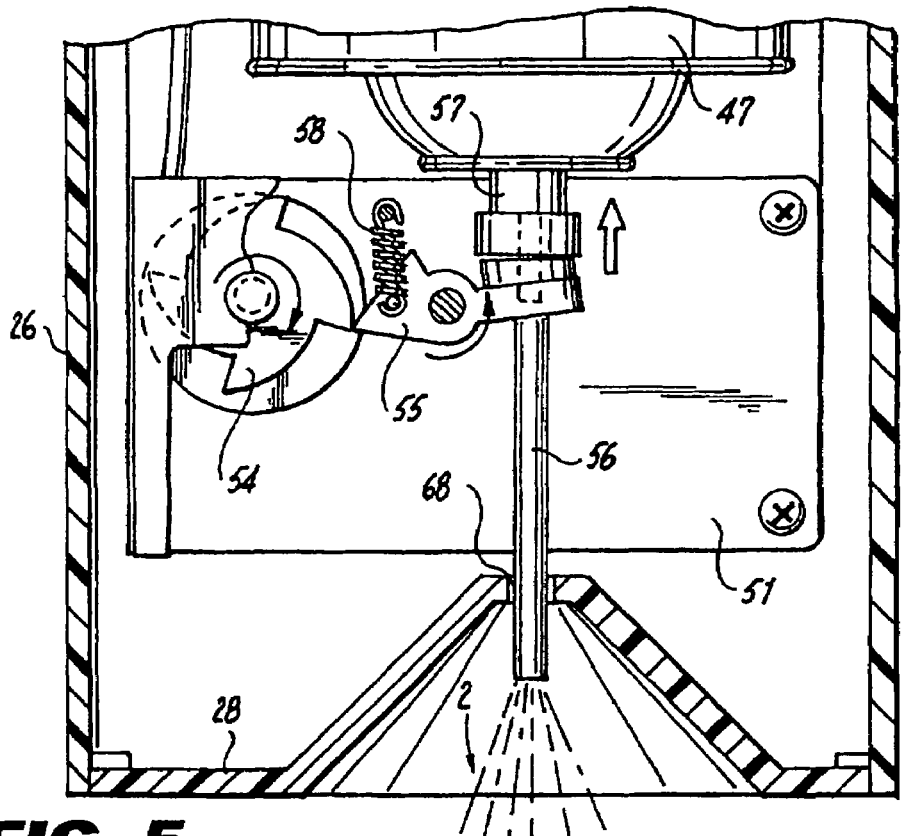
FIG. 5 is a partial enlarged elevation view of a door handle sanitizer absent the outer cover to show interior components.
Figure 6:
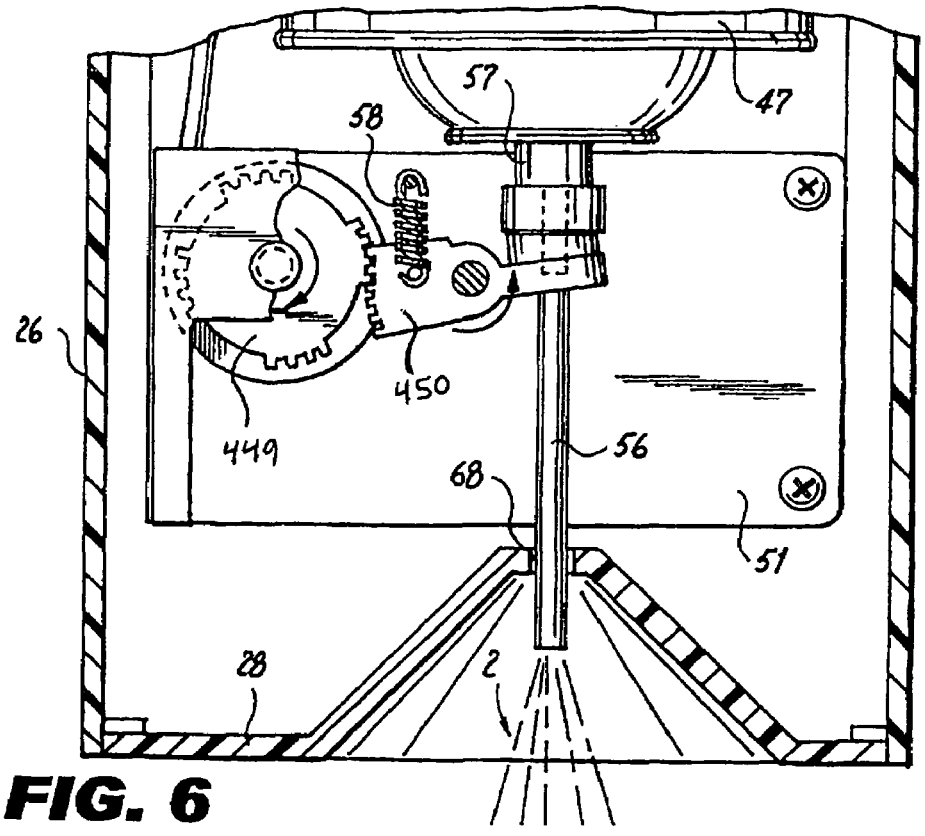
FIG. 6 is a partial enlarged elevation view a door handle sanitizer as in FIG. 5 now showing a variation in the gear arrangement.
Figure 7:
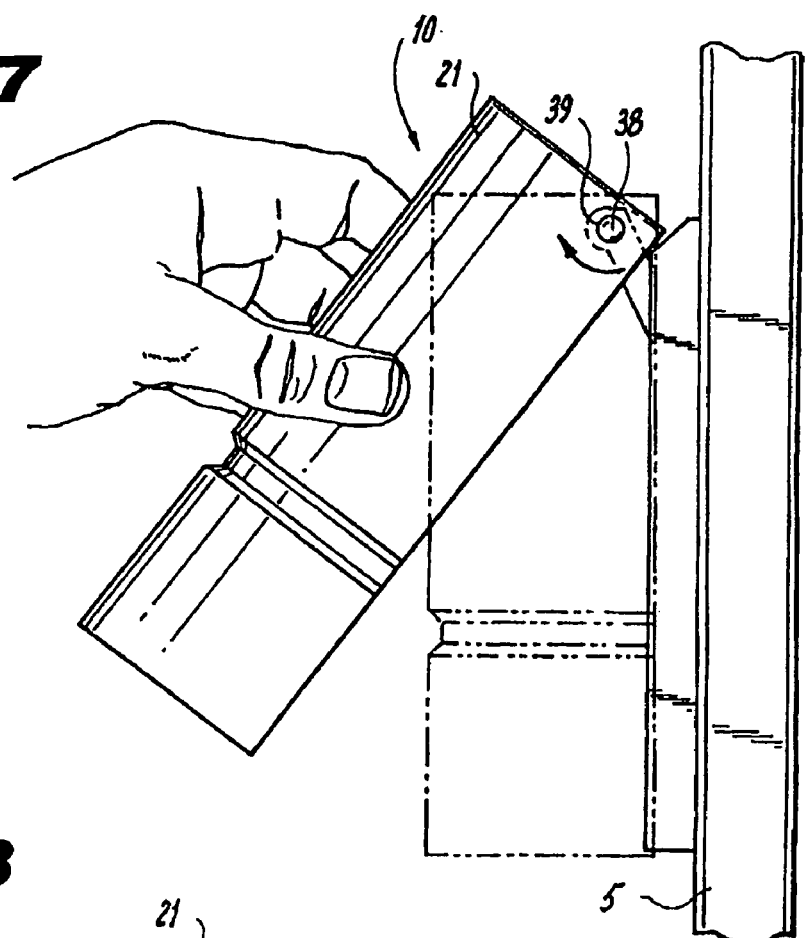
FIG. 7 is a side elevation view of a sanitizer fixed to a portion of a door with its cover opened.
Figure 8:
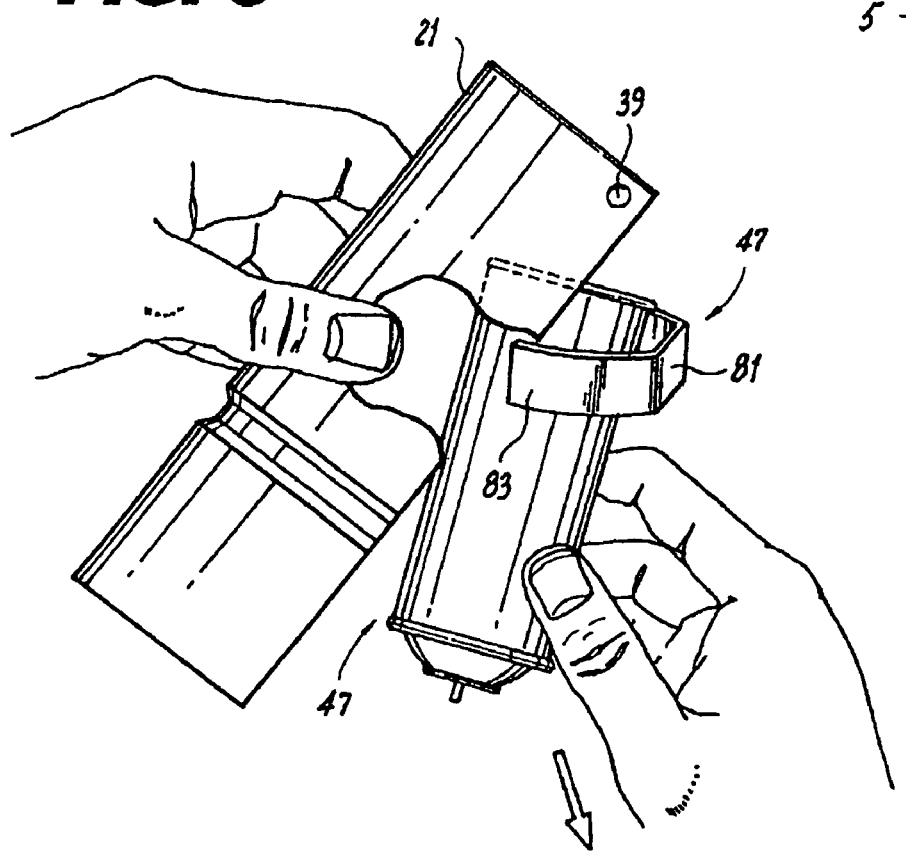
FIG. 8 is a side elevation view of a sanitizer showing removal and replacement of the germicide source.

An arm 55 is pivotally mounted to motor mount 51 and supports the elongated nozzle 56. Valve 57 of germicide source 47 is aligned with and fluidly connected to elongated nozzle 56. Referring to FIGS. 3-5, motor 50 is preferably a DC motor and is operable to rotate a gear 54 clockwise through an angle. The clockwise rotation of gear 54 effectuates a counterclockwise rotational movement in arm 55. Arm 55 moves in synchronization with nozzle 56 and nozzle 56 preferably includes a bearing or frictional surface configured to accept upward driven force from arm 55. Since elongated nozzle 56 is connected to arm 55, the counterclockwise rotation of the arm 55 forces nozzle 56 upward against valve 57 applying a requisite degree of upward force on valve 57 necessary to temporarily open the valve and release germicide 2 contained in source 47 (FIG. 5). The release of germicide 2 from valve 57 flows into elongated nozzle 56 which directs germicide 2 outward from spray dispenser 10 into the surrounding atmosphere and onto handle 14. A spring 58 is fixedly attached between arm 55 and motor mount bracket 51 and is necessary for returning arm 55 to a normal position (shown in FIG. 4) after making contact with and being forced by gear 54.

It should be understood that motor mount bracket 51 supports the components of spray actuator 52 within spray dispenser 10 without impinging the removal of germicide source 47. As shown in FIG. 4, spray actuator 52 is preferably located beneath germicide source 47 and is configured such that elongated nozzle 56 lines up with and partially encompasses valve 57 when germicide source 47 is in place within spray dispenser 10.

Figure 9:
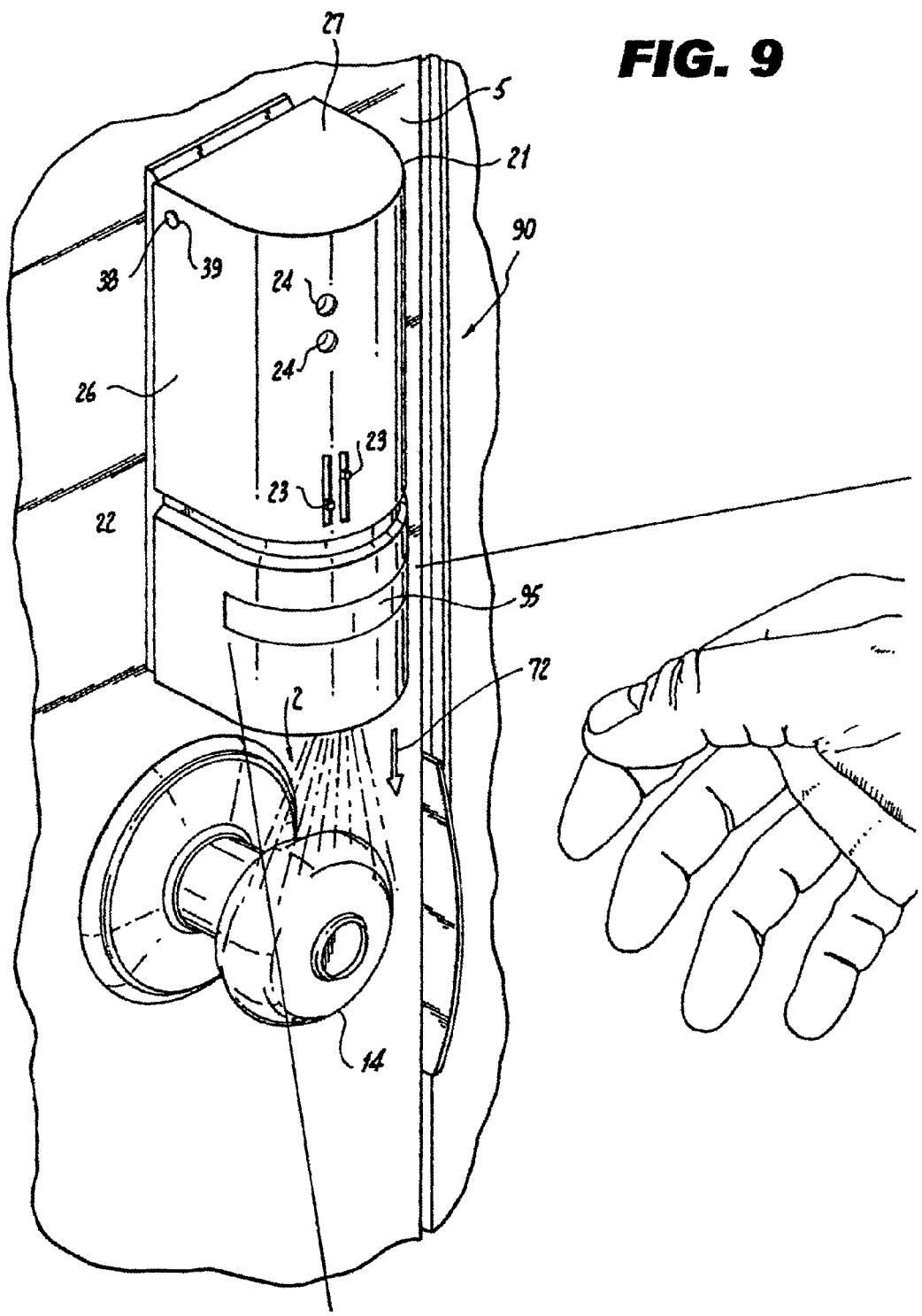
FIG. 9 is a perspective view a door handle sanitizer showing optional further features.

Referring to FIG. 5, gear 54 is preferably configured with equi-distance protrusions or notches along it's peripheral capable of contacting arm 55 and forcing it to pivot as discussed above. Because the forcing of arm 55 by gear 54 results in the opening of valve 57, the longer arm 55 is forced by the gear, the longer valve 57 will remain open and the greater the amount of germicide 2 can be released. The spacing between protrusions on gear 54, the width of each protrusion and the rotational angle through which gear 54 rotates each time motor 50 is activated will all effect how long valve 57 is opened and hence, how much germicidal 2 is released for each given activation. Accordingly, the amount of germicidal released during each activation of spray dispenser 10 can be controlled and an increase or decrease in the amount of germicidal 2 realized by configuring gear 54 so that for each rotation it is contacts and forces arm 55 for a longer or shorter period of time.

In alternative arrangements, the spray activator 52 can be configured with different gears so as to effect a temporary opening of the spray valve 57. Referring to FIG. 6, the equi-distance protrusions on gear 54 of FIG. 5 have been replaced by a series of ribs which correspond to a series of receiving orifices on arm 450. Gear 449 can be configured, by adjusting the size and number of ribs, to allow different time intervals in which force is applied to valve 57. Thus, effecting the amount of germicidal spray released from the valve and ultimately onto the handle. Still in further arrangements the spray activator 52 can be configured to pressurize a dose or ampoule of germicide from a reservoir to release the pressurized fluid as a spray onto the handle 14.

Referring to FIG. 2, component support wall 29 defines a battery-containing compartment 44 at a top marginal edge thereof for supporting two AA batteries 45 and includes a control circuit 31 mounted thereto for receiving signals from switches 23, processing the received signals and controlling indicator lights 24 and motor 50. Control circuit 31 is operable to trigger optional indicator lights 24 during the operation of spray dispenser 10, signaling the user of such occurrences as when switches 24 or spray dispenser 10 have been activated. Control circuit 31 is preferably preprogrammed to activate motor 50 at prescribed intervals which are determined by setting switches 23. For instance, switches 23 define a variety of user selectable time intervals and, in response to a specific switch setting, control circuit 31 supplies power to motor 50 at certain intervals. Each time motor 50 is powered it will trigger spray actuator 52 and release germicide 2 from source 47. Since it is known and fairly common that any microcontroller capable of controlling and processing signals indicative of operational time intervals may generally be used, the particular implementation of control circuit 31 has been omitted for clarity. Conventional wires connect control circuit 31 to power (supplied by batteries 45), indicator lights 24, user operable control switches 23 and motor 50.

Referring to FIGS. 4 and 5, elongated nozzle 56 is aligned with a through hole 68 on bottom wall 28 of the housing 21. Through hole 68 functions as an access point through which elongated nozzle 56 exits housing 21. The elongated nozzle 56 is fluidly connected to the germicide source 47 via valve 57 to receive germicide therefrom and is oriented to spray germicide in axial dimension A of housing 21 (FIG. 1) away from the bottom wall 28 of the housing 21 and toward handle 14 of the door 5. This outwardly directed spray 72 should be of a force and breadth to completely cover at least half the entire perimeter 15 of handle 14.

Referring to FIG. 2, installation of spray dispenser 10 begins by first positioning base 22 proximate to the door handle 14 (e.g., above the door handle on the door itself) and securing it to the door via screws 35. Next, component support wall 29 is mounted to base 22 using any conventional securing or locking means, such as screws, glue, Velcro, clips, snap-fit arrangements, etc. Finally, batteries 45 are inserted in battery compartment 44, germicide source 47 is inserted into mounting bracket 49 and outer cover 21 is fixedly attached to base 22 at support prongs 38. Outer cover 21 can now be closed providing complete cover for support wall 29 and the components thereon and spray dispenser 10 activated.

As further illustrated with reference to FIGS. 7 and 8, prongs 38 are configured to rest within orifices 39 of outer cover 21 and provide pivotal movement of the cover about the prongs 38, thereby permitting "opening" of spray dispenser 10 by pivoting cover 21 away from support 22 and "closing" of spray dispenser 10 by pivoting cover 21 toward support 22. Thus, complete access to both battery compartment 44 and germicide source 47 can be achieved. Optionally, the cover and support can be severed to one another with a lock or keyed release so as to prevent tampering by unauthorized individuals.

The germicide 2 contained in source 47 and sprayed on the handle 14 can comprise a disinfecting liquid, aerosol, mist or the like, and is preferably characterized by it's ability to sanitize surfaces it comes into contact with. According to alternative embodiments of the present of invention, germicide 2 comprises a chlorine-based chemical solution as this provides a relatively non-flammable fluid (as compared to an alcohol-based solution) and also provides the germicide function discussed above. It is to be understood that the term "germicide" used herein is not intended to be limited to any particular type of chemical solution or fluid and the scope and meaning of this term includes any suitable fluid or composition which acts as a disinfectant. Optionally, a scent additive may be included in the fluid in order that the sanitizing fluid may also function as an air freshener.

In certain instances, such as with room doors and the like, the spray dispenser 10 dispenses germicide 2 at certain given intervals in time, for example by a time switch, clock control, and the like. According to alterative aspects of the invention, the spray actuator 52 can be triggered in response to manipulation of the door handle 14, such as after each individual manipulation or following a given series of such manipulations. In the latter case, a counter can initiate the release of germicide 2 whenever a predetermined count is reached. Such cases just cited are all examples of a controlling software program. It is this software program that is responsible for automating the disinfecting methods disclosed earlier, by activating the handle sterilization process when a predetermined state or function is sensed.

Referring to FIG. 9, optional further features are shown in which the front wall 26 further comprises a sensor 95 for triggering spray actuator 52. Sensor 95 can be optical, infrared, mechanical/electrical or a combination of the above. Thus, in this arrangement the actuator 52 can activate the spray when a person or movement is detected in a vicinity of the handle or when a light beam interruption or vibration is detected. Alternatively, sensor 95 can be used to disable the spray mechanism or turn off the unit for a specific period of time, rather than to activate the spray mechanism. For example, spray dispenser 10 can be controlled to dispense germicide 2 at certain given intervals in time as discussed above and sensor 95 can serve to disable the spray dispenser when a certain condition is sensed by the sensor, for example, sensor 95 can comprise an optical sensor and be triggered to suppress further spraying when the lights are turned off or a person is close to the unit.

Figure 10:
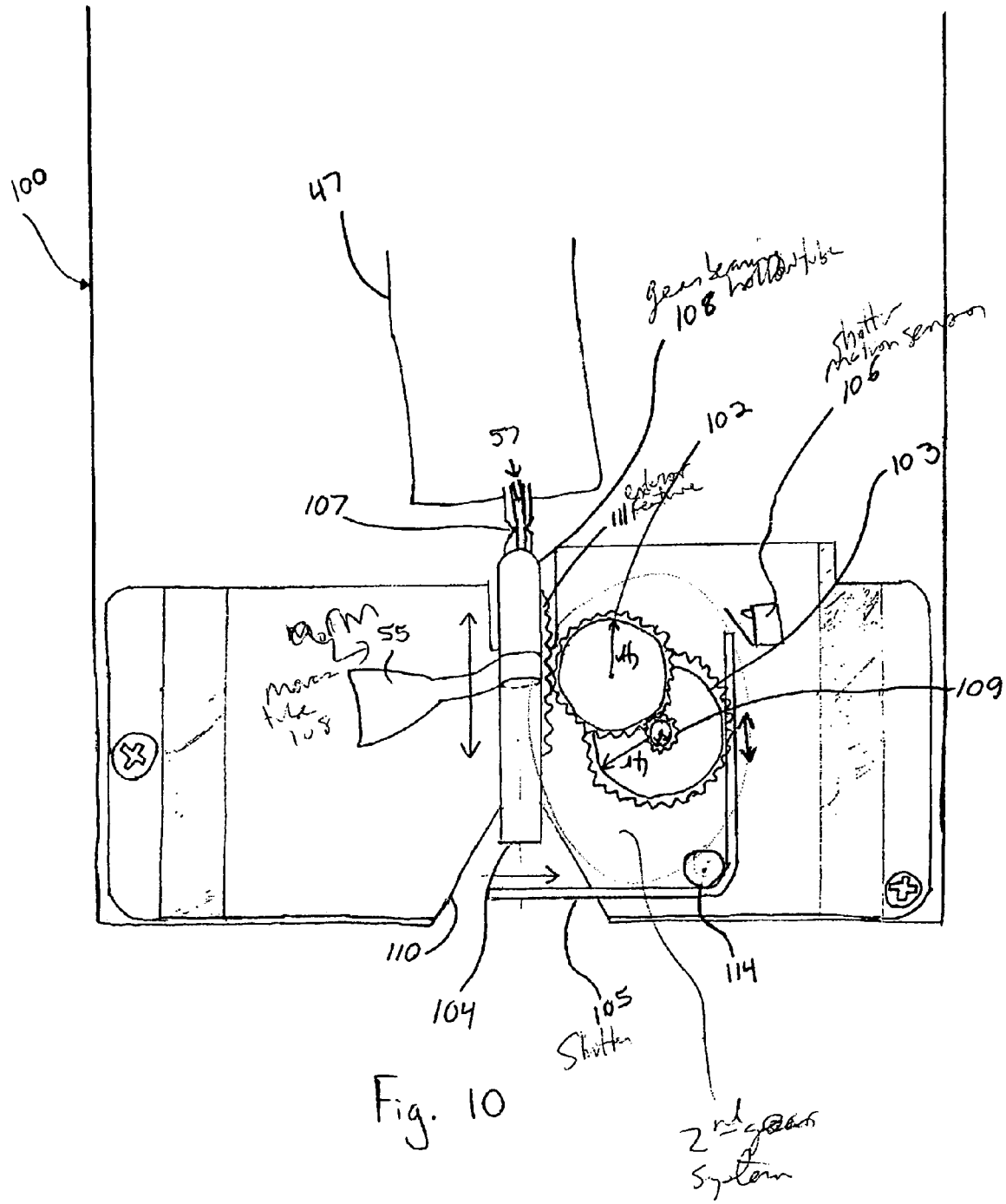
FIG. 10 is a front elevation view of a door handle sanitizer, absent the outer cover, to show optional further interior components.

Referring to FIG. 10, a front elevation view of a door handle sanitizer 100 having further, optional features is shown. As in the door handle sanitizer illustrated in FIG. 3, Door handle sanitizer 100 includes a motor 50 and a first gear system comprising gears 54 and 55. Referring to FIG. 10, further features include a second gear system comprising spray gears 102, 103 and 109, a mechanical shutter 105, shutter motion sensor 106, nozzle 104, frangible joint 107, spindle 114 and gear-bearing hollow tube 108. As shown, the second gear system is isolated from the first gear system yet coupled thereto by the attachment. Further, the shutter 105 and motion sensor 106 are provided to block the aerosol spray unless gears 102, 103 and 109 are set in motion by track 111 on gear-bearing tube 108. Gear-bearing tube 108 conveys aerosol from valve 57 of aerosol can 47 to nozzle 104, into conical opening 110 and outward from spray device 100.

Shutter 105, when positioned at rest, blocks the exit of aerosol spray from nozzle 104. Tube 108 and spray valve 57 move vertically (as illustrated) in a reciprocal motion, meaning each time tube 108 is forced into motion by arm 55 (as discussed with respect to FIG. 5), tube 108 and valve 57 are forced toward aerosol can 47, resulting in a momentary spray of aerosol from the can. Valve 57, nozzle 104 and tube 108 are fluidly connected such that aerosol spray exiting valve 57 travels through the tube 108 to nozzle 104 before discharging from the housing of the door handle sanitizer 100.

Gears 102, 103 and 109 cooperate with the movement of tube 108 and have a ratio of movement chosen to result in rapid movement of shutter 105 so as to clear a path for the aerosol spray in response to a comparatively smaller reciprocal movement of the tube 108. An exterior feature (track 111) disposed on tube 108 moves synchronously with tube 108. Track 111 can comprise a series of bearing surfaces, e.g., teeth, grooves or slots, which are operable to engage with corresponding receiving features on gear 102. When tube 108 is forced upward by arm 55, track 111 sets gear 102 into a clockwise rotation. Gear 103 is mechanically engaged, via gear 109, between gear 102 and shutter 105 and responds to movement of gear 102 by rotating counter-clockwise and forcing movement of shutter 105. Gear 109 is preferably at least two magnitudes smaller than gears 102 and 103 and is fixedly mounted to gear 103 to provide a mechanical advantage, such that a small translation of tube 108 in the vertical direction results in a large translation of shutter 105 in relation to conical opening 110. This is necessary for shutter 105 to overcome at least a good portion of the distance of conical opening 110, which is a larger distance than the tube 108 moves in the vertical direction. The resulting effect of the counter-clockwise movement of gear 103 is to force shutter 105 to its displaced position such that it unblocks conical opening 110 allowing aerosol spray to exit there through. This is accomplished by including a bearing or frictional surface on a portion of the side of shutter 105 in communication with gear 103 such that the forced rotation of gear 103 moves shutter 105. One of ordinary skill in the art will realize that any general pattern of apertures can be disposed on shutter 105 as long the apertures are capable of mating with corresponding apertures on gear 103.

Shutter 105 includes a flexible portion or component extending outward from its midpoint and is therefor operable to flex about spindle 114 as it is set into motion by gear 103, as described above. Since tube 108 is recessed, a conical opening 110 on housing 100 is preferred so that aerosol spray has an even dispersion pattern when exiting the housing.

After tube 108 has been activated, causing aerosol spray to discharge from spray dispenser 100, tube 108 will return to its rest position reversing the movement of gears 102, 103 and 109, thereby causing shutter 105 to return to its rest position (e.g., to close conical opening 110). The downward motion of tube 108 is the same as previously described except all gears move in the reverse direction.

Sensor 106, embodied as a switch in FIG. 10, is positioned so as to detect movement of shutter 105 and exposure of the nozzle 104. When gear 103 is set into motion, it moves shutter 105 into contact with sensor 106. Sensor 106 is connected to control circuit 31 (FIG. 2) and sends a movement signal to the control circuit in response to being triggered by movement of shutter 105. This movement signal is indicative of the fact that shutter 105 has moved a predetermined amount suitable to be sensed by the sensor 106. The sensor can comprise a mechanical switch, but one of ordinary skill in the art will realize that other types of sensors can be used in place of a mechanical switch, e.g., electromechanical, optical or magnetic sensors. Regardless of the type of sensor 106 employed, it must be positioned and/or configured such that it is operable to detect at least movement of the shutter in one direction (e.g., each opening of the shutter).

Door handle sanitizer 100 further includes software programmed in control circuit 31 or elsewhere within the spray dispenser to monitor any sensed shutter 105 movement. One way for the software to monitor sensed shutter 105 movement is by testing for a state change in sensor 106. In accordance therewith, sensor 106 can be configured to go from an open state to closed state and from the closed state back to the open state in one spray cycle. If such state changes in sensor 106 do not occur in a specified time frame, it can be inferred that the mechanisms of door handle sanitizer 100 have either failed, been tampered with or a non-approved aerosol can is being used, in which case further spray cycles can be suspended by the software. The software preferably comprises a timing circuit to determine shutter 105 movement necessary to continue to permit triggering of the aerosol spray. In accordance with a salient aspect of the present invention, the timing circuit can be overridden by an optical proximity sensor (not shown) which, as discussed above with respect to sensor 95 of FIG. 9, can be used to disable sanitizer 100 under certain conditions, e.g., off peak hours of operation.

A reset can be built into the software which resets control circuit 31 so as to reactivate the circuit after spray cycles have suspended. The reset can be activated mechanically in which case an authorized person can manually trigger a reset switch on the housing (not shown). Alternatively, the reset can be automatically programmed into the software so as to automatically reset control circuit 31 to resume spray cycles after a prescribed time of inactivity due to lack of a movement signal being provided to the software.

In accordance with another aspect of the present invention and with continued reference to FIG. 10, tube 108 connects to valve 57 of aerosol can 47 using a strong adhesive, epoxy or heat seal (e.g. a melt bond) and is connected so as to prevent separation of the tube 108 from the valve 57. A frangible joint 107 is disposed between a first end of the tube 108 and the track 111 and is provided to weaken the connection therebetween. Frangible joint 107 is preferably formed in the material of the tube 108 but can comprise a separate element in the joint 107 is constructed with a weak portion so as to break the tube 108 at a location near aerosol can spray valve 57 should someone attempt to disconnect tube 108 from valve 57. Preferably, the frangible joint 107 includes a score, perforation, break-line, or any other feature that is weaker than the bond between the valve 57 and the tube 108. Frangible joint 107 acts as a security feature should a person attempt to disconnect aerosol can 47 from tube 108 and reuse it with another can. Its construction is operable to break the tube 108 and shorten its overall length, rendering it incapable of driving gear 102, in the event that the tube is thereafter reattached to another valve 57, because the track 111 will no longer align with the gear 102.

Figure 11:
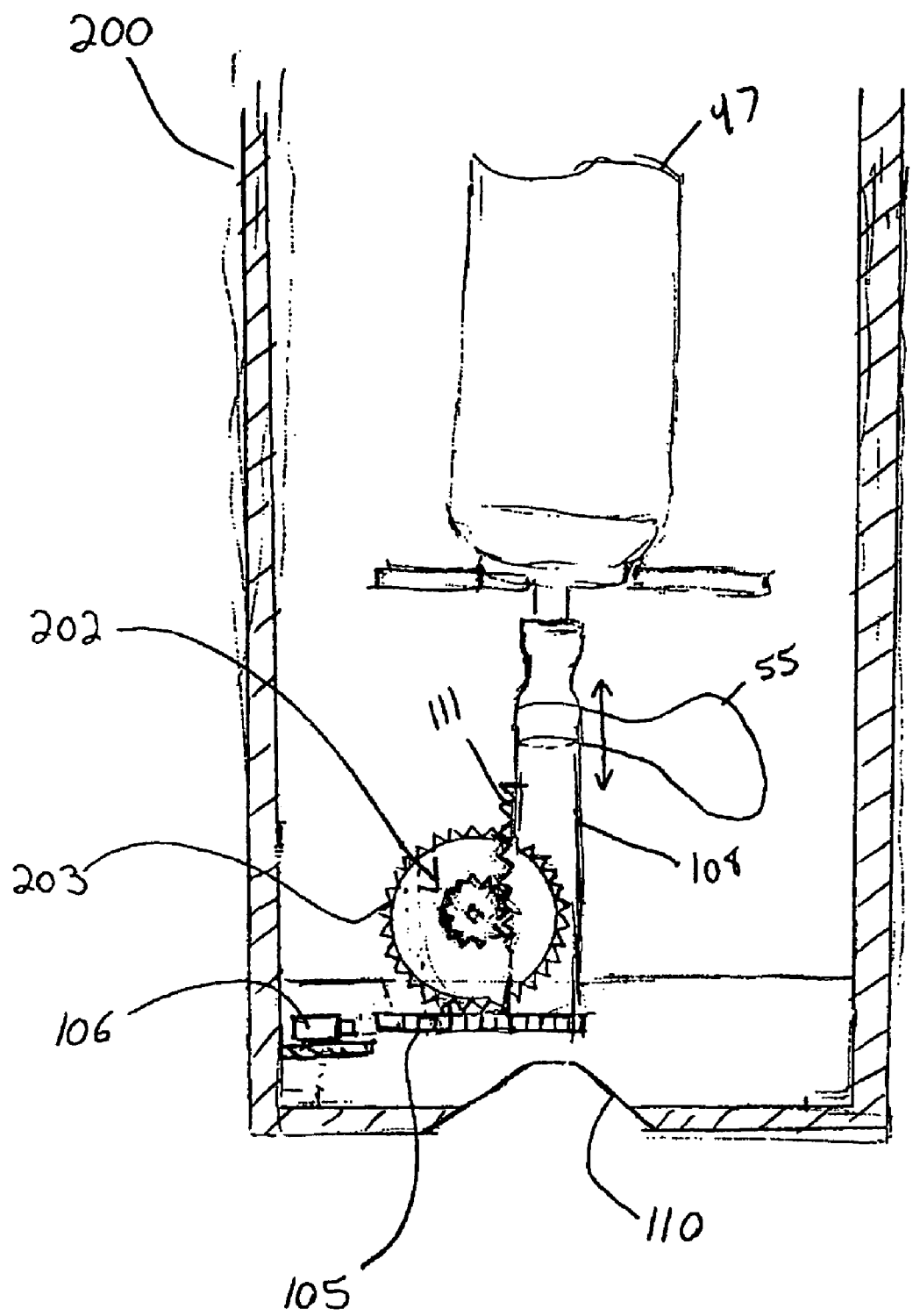
FIG. 11 is a front elevation view of a door handle sanitizer, absent the outer cover, to show optional interior components in accordance with a variation of FIG. 10.
Figure 12:
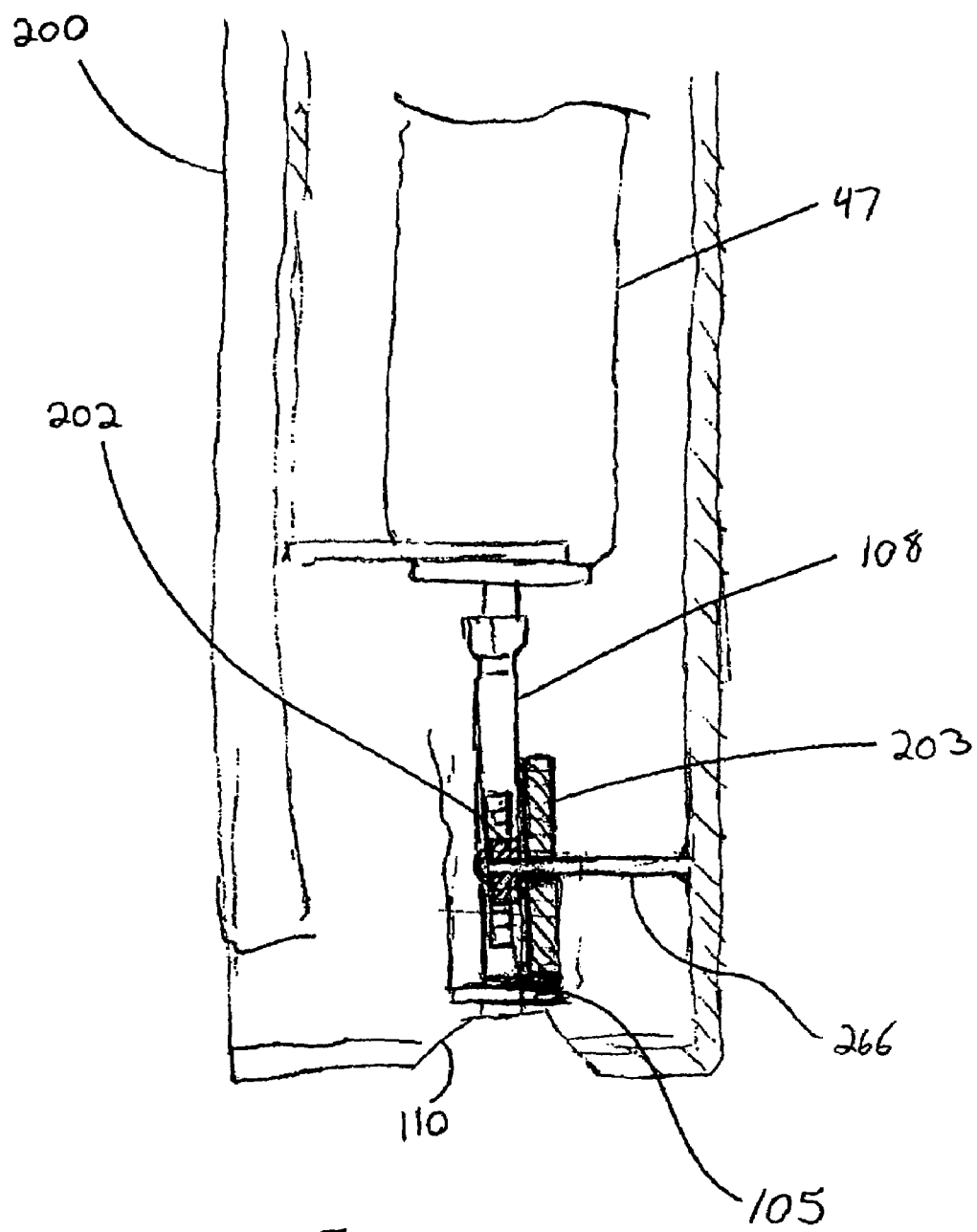
FIG. 12 is a side elevation view of a the door handle sanitizer of FIG. 11.
Figure 13:
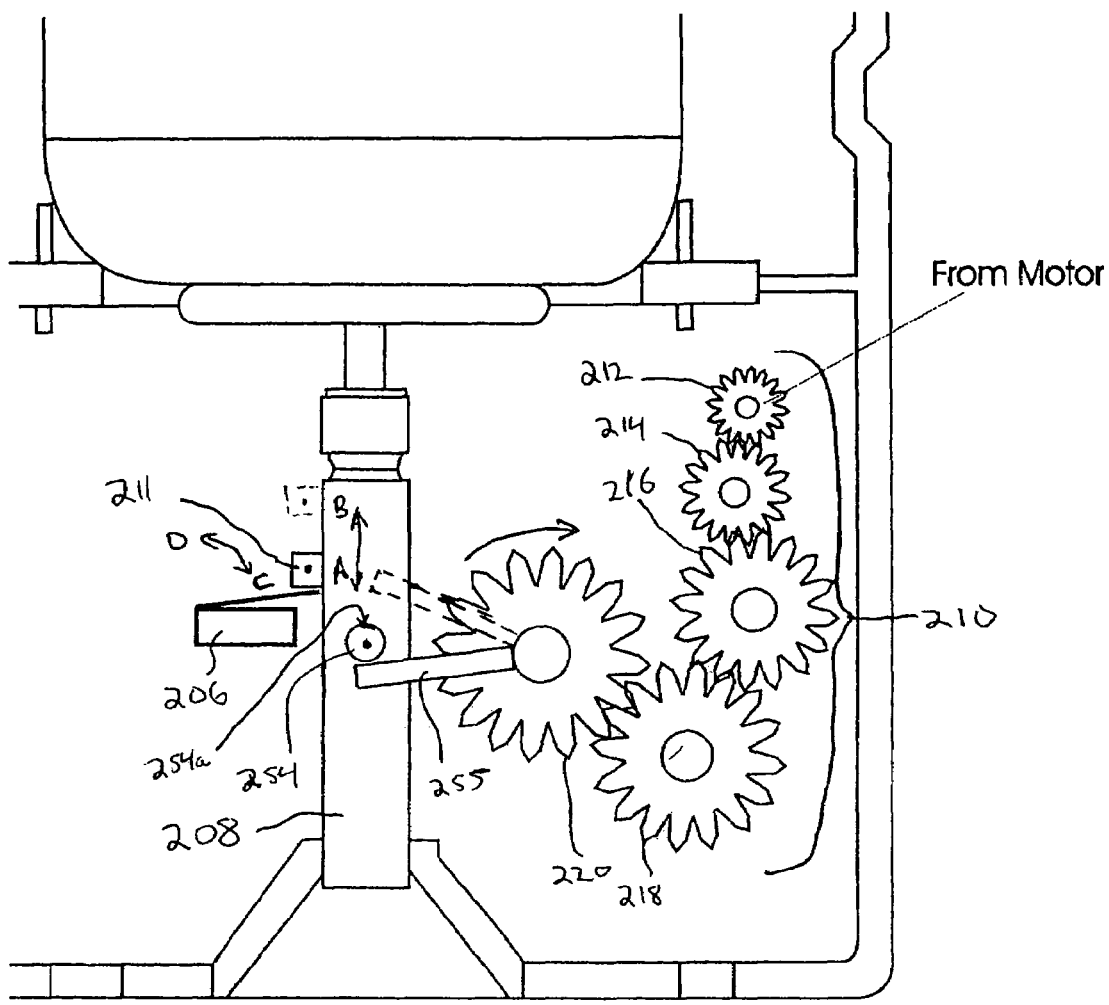
FIG. 13 is a front elevation view of a door handle sanitizer, absent the outer cover, illustrating an arrangement and cooperation of a valve attachment with surrounding mechanical and electrical elements.

FIGS. 11 and 12 are respective front and side views of a door handle sanitizer 200 according to an alternative arrangement of the one illustrated and described in FIG. 10 above. The alternative arrangement illustrated in FIGS. 11-12 includes all of the components described above with respect to FIG. 10 with the exception of the spindle 114, and is arranged in a more compact form, requiring one less gear. Door handle sanitizer 200 includes gears 202 and 203, mechanical shutter 105, shutter sensor 106, nozzle 104, frangible joint 107 and gear-bearing tube 108. The shutter 105 and motion sensor 106 functions remain the same, namely, to block the aerosol spray unless gears 202 and 203 are set in motion by track 111 on gear-bearing tube 108. Gear-bearing tube 108 conveys aerosol from valve 57 of aerosol can 47, through conical opening 110, outward from spray device 200 via the nozzle 104.

Gears 202 and 203 cooperate with the movement of tube 108 resulting in rapid movement of shutter 105 so as to clear a path for the aerosol spray to emit from the nozzle. A track 111 disposed on tube 108 moves synchronously with tube 108. Track 111 comprises a feature suitable for moving the gears, e.g., teeth, grooves or slots, which are operable to engage with corresponding receiving features of gear 202. When tube 108 is forced upward by arm 55 track 111 sets gear 202 into a counter-clockwise rotation. Gear 203 is fixed to gear 202 and is at least two magnitudes larger in diameter and preferably four magnitudes larger. Accordingly, gears 202 and 203 move together. Gear 203 engages shutter 105 forcing the shutter to move horizontally when the gear is in motion. The resulting effect of the counter-clockwise movement of gears 202 and 203 is to move shutter 105 such that it unblocks conical opening 110 allowing aerosol spray to exit there through. Since tube 108 is recessed, a conical opening 110 on housing 100 is preferred so that aerosol spray has a proper dispersion pattern when exiting the unit. A bearing or frictional surface on a portion of the side of shutter 105 in communication with gear 203 is preferred such that the forced rotation of gear 203 drives movement of the shutter 105. Raised features or apertures configured to engage the gear 203 can also be employed to engage and move the shutter.

Similarly to the discussion following FIG. 10, after tube 108 has been activated causing aerosol spray to discharge from spray dispenser 100, the tube 108 will return to its rest position reversing the movement of gears 102, 103 and 109, thereby causing shutter 105 to generally overlie the axis of the tube 108 and the nozzle 104, and perhaps close conical opening 110. Sensor 106, embodied as a switch, is positioned so as to detect movement of shutter 105.

Referring now to FIG. 13, the cooperation of a sensor 206 with movement of a hollow delivery tube 208 is described to illustrate for the aspects in accordance with certain aspects of the invention. Sensor 206 and tube 208 can be of the same construction as sensor 106 and tube 108. In the arrangement shown in FIG. 13, energy from the motor 50 (not shown; see FIG. 3) is conveyed to a protruding bearing surface 254 supported by the delivery tube by a driven arm 255. The arm is pivoted or rotated in response to a gear 212 that is placed in rotation with activation of the motor. The motor is activated by the control circuit 31 described above, typically by a voltage applied across the motor terminals ("energization signal"). Preferably, the energization signal is a DC voltage.

As illustrated, a first gear system 210 comprising gears 212-220 are positioned and sized so as to move the arm 255 in a clockwise rotation (see arrow). With rotation of the arm 255, a generally axial (upward) force is imparted to the bearing surface 254 to cause the tube 208 to reciprocally move upward and open the valve 57 of the aerosol can. The valve opens only momentarily because continued rotation of gear 220 advances pivot arm 255 to the position shown in broken lines beyond and clear of the bearing surface 254. The arm can continue to rotate to a rest position, after the motor stops driving the gear system 210, such as at, say the 8 o'clock position. Once the pivot arm has moved past the bearing surface 254, the tube 208 returns to its rest (downward) position (as shown) in which the valve 57 is closed. The pressure in the aerosol can biases the valve to position the delivery tube in the rest position. The gear system 210 can comprise multiple gears or just one gear.

Movement of the delivery tube in an axial direction includes a synchronous movement of an exterior feature associated with the tube. The exterior feature can be a portion of the bearing surface 254 (such as segment **254*a* on an opposite side from where the arm 255 contacts the bearing surface), but is illustrated as a separate exterior feature 211. Exterior feature 211 has a rest position A when the tube is disposed such that the valve 57 is closed (the downward position) and a displaced position B when the tube has been urged by the arm 254 to the open-valve position (the upward position) with a concomitant displacement of the tube 208. When the sensor 206 comprises a mechanical switch, the exterior feature 211 alternately depresses the mechanical contact of the sensor (position C) or permits release of the mechanical contact (position D) as a function of the position of the delivery tube 208. A bias, not shown, normally urges the contact switch toward position D, in a conventional manner. Thus, the reciprocal movement of tube 208 causes alternate state changes of sensor 206 as the contact moves between positions C and D (at that moment or thereafter). As can be appreciated, the sensor 206 can take forms other than a mechanical switch (e.g., an opted sensor or a vibration sensor or a sound sensor) with the exterior feature 211 adapted to cause a state change which is detected in synchronization with movement of the tube 208. The state change sensed by the sensor delivers control signals to the control circuit 31**. Software executing within a processor of the control circuit can be configured to react to the presence or absence of the state signals, generally, and more particularly in relation to other events such as the timing of receipt of such signals relative to delivery of the motor energization signal or a particular time interval. In the event that the state signals are not generated during a motor actuation cycle, the control circuit can inhibit delivery of further motor energization signals, or not generate such motor energization signals any longer.

As can be appreciated from the foregoing, software resident in the control unit 31 is in electrical communication with the sensor 206 in order to confirm or determine whether the state of the sensor is changing with each actuation of the motor, and hence, with each dose of the aerosol spray. Preferably, the system has logic in the control unit which is programmed to energize the motor and cause the first gear system 210 to reciprocally move the tube 208 only if the sensor registered a state change on the prior actuation of the motor. This ensures that an appropriate aerosol source has been properly loaded in the dispenser. The logic of control unit 31 can enable one or more sprays without a state change having been detected, for example, just after closing the dispenser lid.

Thus, sensor 206 senses the movement of the tube 208 through its cooperative arrangement with external feature 211. The sensor transitions between closed and open states and between open and closed states with reciprocal movement of the delivery tube 208. These state changes are expected by the control unit 31 to occur within a time interval (e.g., 300 ms) corresponding to one spray cycle or to be detected while the motor drive signal is being applied to the motor. This enables the the logic unit to react in the event that signals are not as expected, for example, if the aerosol can and its delivery tube 208 are not properly loaded within the dispenser housing.

The control unit 31 can suppress further motor actuations if the sensor 206 does not deliver state change signals. The motor actuation cycle can also be suppressed if certain external conditions are detected such as the presence of a hand of a person in the vicinity of the sanitizer unit 200.

Referring again to FIG. 1, handle 14 can take any shape or size and is preferably configured to assist in opening and closing of door 5. Handle 14 can be of a stationary type used to push or pull door 5 or can be mechanically mounted and include a conventional locking mechanism, requiring rotation of a handle to unlock the door prior to opening and closing. While the handle is illustrated as a conventional cylindrical shaped door handle, the spray dispenser 10 described herein is operable to sanitize any door handle and examples of several handle shapes which can be sanitized by spray dispenser 10 include, but are not limited to, spherical, rectangular, hexagonal, rod or hook-shape handles and composites thereof. Handle 14 has a knob portion 13 comprising an outer perimeter 15 and a diameter dimension D which extends through the center of knob 13 to the outer perimeter 15. One of ordinary skill in the art would realize that door 5 can be handless, and in place of the handle a flat plate could be affixed to the surface of the door for pushing or pulling the door. As described in greater detail below, the embodiments of spray dispenser 10 described herein can be equally applied to such plate arrangements by orientating nozzle 56 to direct the germicide spray onto a plate-type arrangement as opposed to a protruding handle 14.

Although the embodiments of the invention were described with reference to a disinfection apparatus for restroom doors it should be noted that at least some of the embodiments are suitable also for disinfecting other kinds of handles, such as handles of cabinets for the sterile storing of surgical instruments, doors of operating theaters or rooms in hospitals etc.

Expedients of the present invention described in one embodiment are not to be limited to that embodiment and can be readily combined with any of the other described embodiments. Furthermore, any feature of one embodiment, not expressly described in connection with an alterative arrangement or embodiment, can be combined with that arrangement or embodiment to derive benefit there from.

While the invention has been described with reference to several embodiments thereof, the invention is more broadly defined and limited only by the recitations in the claims appended hereto and their legal equivalents.

I claim:

1. A system for controllably dispensing an aerosol sanitizer onto a door handle, the sanitizer being contained in a replaceable aerosol can having a valve and a delivery tube in fluid connection therewith, the delivery tube being seated on the valve and having a remote nozzle through which the aerosol sanitizer is sprayable, comprising:
   a housing sized to seat the aerosol can therein;
   a motor;
   a control circuit having a processor configured to selectively energize the motor with an energization signal;
   a first gear system coupling the motor to the delivery tube and arranged so that energization of the motor moves the first gear system which then displaces the delivery tube so as to momentarily open the valve of the aerosol can;
   a sensor disposed within the housing and responsive to displacement of the delivery tube to deliver state signals to the control circuit;
   wherein the control circuit includes software executing within the processor and configured to prevent delivery of the energization signal in the event that the state signals fail at least one prescribed condition.

2. The system of claim 1, wherein the sensor has a rest position and a displaced position and wherein the sensor delivers a state signal after a change from one of the rest and displaced positions.

3. The system of claim 1, wherein the at least one prescribed condition is receipt of the state signals.

4. The system of claim 1, wherein the at least one prescribed condition is receipt of the state signals within a prescribed time interval.

5. The system of claim 1, wherein the at least one prescribed condition is receipt of the state signals while the energization signal is present.

6. The system of claim 1, wherein the delivery tube includes an external feature supported thereby and wherein the sensor delivers the state signals in response to displacement of the external feature.

7. The system of claim 6, wherein the external feature supported by the delivery tube is a protuberance that mechanically interacts with the sensor.

8. The system of claim 6, wherein the sensor detects displacement of the external feature by one of an optical detector, a vibration detector, or a sound detector.

9. The system of claim 6, wherein the external feature is supported by the delivery tube so as to move in synchronization with any displacement of the delivery tube.

10. The system of claim 1, wherein the delivery tube includes a bearing surface and wherein the first gear system couples the motor to the delivery tube by bearing upon the bearing surface.

11. The system of claim 1, wherein the housing has an open position for loading the aerosol can and a closed position, the system further comprising a means for mounting the housing to a door, the mounting means being accessible when the housing is in the open position.

12. The system of claim 1, wherein the first gear system is coupled to the delivery tube so that the momentarily opening of the valve of the aerosol can conveys a generally prescribed amount of aerosol sanitizer onto the door handle.

13. The system of claim 1, wherein the control circuit includes a timing program which delivers the engerization signal at a prescribed time interval.

14. The system of claim 13, further comprising a manual switch within the housing connected to the control circuit so as to establish the prescribed time interval at one of a plurality of settings.

15. The system of claim 1, further comprising a second sensor connected to the control circuit so as to prevent delivery of the engerization signal based on an absence or occurrence of a condition exterior to the housing.

16. A method for ensuring proper loading of an aerosol can within a dispenser, the aerosol can containing a sanitizer, comprising the steps of:

automatically displacing a delivery tube connected to a valve of the aerosol can to open the valve and dispense the sanitizer through and from the delivery tube at an interval and free of any manual activation;

registering at least the displacement of the delivery tube using a sensor;

preventing subsequent automatic displacement of the delivery tube at the interval in the event that the sensor has not registered at least the displacement of the delivery tube.

\* \* \* \* \*